United States Patent [19]
Herzig et al.

[11] Patent Number: 5,691,435
[45] Date of Patent: Nov. 25, 1997

[54] CROSSLINKABLE COMPOSITIONS

[75] Inventors: Christian Herzig, Waging am See; Bernward Deubzer, Burghausen; Martina Bloechl, Tann; Robert Banfic, Burgkirchen, all of Germany

[73] Assignee: Wacker-Chemie GmbH, Munich, Germany

[21] Appl. No.: 782,871

[22] Filed: Jan. 14, 1997

[30] Foreign Application Priority Data

Jan. 25, 1996 [DE] Germany .................. 196 02 663.6
Aug. 8, 1996 [DE] Germany .................. 196 31 936.6

[51] Int. Cl.⁶ .................................................. C08G 77/08
[52] U.S. Cl. ...................... 528/15; 528/9; 528/12; 528/23; 528/31; 528/25; 528/18; 528/21; 528/20; 525/478; 525/479
[58] Field of Search .................. 528/15, 23, 31, 528/12, 25, 9, 20, 21, 18; 525/478, 479

[56] References Cited

U.S. PATENT DOCUMENTS 5,264,522 11/1993 Mize et al. .................. 528/15
5,635,578 6/1997 Arai et al. .................. 528/15

FOREIGN PATENT DOCUMENTS 0549343 6/1993 European Pat. Off. .

OTHER PUBLICATIONS

Chemical Abstracts, vol. 121, No. 10, 5 Sep. 1994, Columbus, Ohio US; abstract No. 1106692, Ito, H. et al.
Chemical Abstracts, vol. 121, No. 15, 10 Oct. 1994, Columbus, Ohio US; abstract No. 179863a, Sato, S. et al.
Chemical Abstracts, vol. 69, No. 15, 7 Oct. 1968, Columbus, Ohio US, abstract No: 59321h, Andrianov, K. A.
Journal of Polymer Science, Part A: Polymer Chemistry Bd. 32; Nr. 4., 1994 pp. 683–697: XP002025640, Crivello, J. V. et al.
Chemical Abstracts, vol. 123; No. 5, 31 Jul. 1995 Columbus, Ohio US; abstract No. 56277w, Yamamoto, Y. et al.
Chemical Abstracts, vol. 123, No. 10, 4 Sep. 1995 Columbus, Ohio US, abstract No. 114070m, Kosakai, S.

*Primary Examiner*—Melvyn I. Marquis
*Attorney, Agent, or Firm*—Martin Connaughton

[57] ABSTRACT

The present invention provides crosslinkable compositions comprising
(A) an organosilicon compound having radicals containing aliphatic carbon-carbon multiple bonds,
(B) an organosilicon compound having Si-bonded hydrogen atoms,
(C) a catalyst which promotes the addition of Si-bonded hydrogen onto aliphatic multiple bond, and optionally
(D) an agent which retards the addition of Si-bonded hydrogen onto aliphatic multiple bond at room temperature and to the use of the crosslinkable compositions for producing coatings which repel tacky substances.

The present invention also relates to organosilicon compounds having Si-bonded hydrogen atoms, and to a process for their preparation.

7 Claims, No Drawings

CROSSLINKABLE COMPOSITIONS

BACKGROUND OF THE INVENTION

The present invention relates to organosilicon compounds having Si-bonded hydrogen atoms, and to a process for their preparation.

The crosslinking agents typically used for aliphatically unsaturated organopolysiloxanes are mostly organopolysiloxanes containing hydridomethylsiloxane units, the simplest being hydridomethylpolysiloxane which is end-blocked with triorganosiloxy groups. To increase the reactivity, dimethylsiloxane units and hydridomethylsiloxane units are incorporated by equilbration. These measures, however, are limited improvements.

In addition to the crosslinking agents based on hydridomethylsiloxane units, those without methyl groups are also known. DE-B 1 955 511 and corresponding cl.S. Pat. No. 3,615,272 describe resins comprising hydridosiloxane units, i.e. trifunctional units. However, polymers of this kind are restricted for use in addition-curing organopolysiloxane compositions as crosslinking agents, since they are virtually insoluble in the crosslinkable diorganopolysiloxanes.

EP-A 568 318 discloses organopolysiloxanes comprising trifunctional siloxane units and monofunctional siloxane units containing Si-bonded hydrogen. In accordance with EP-A 568 318, T units in the form of organosiloxane units are end-blocked with hydridodimethylsiloxy groups, and between these groups it is possible to incorporate a different number of dimethylsiloxane or hydridomethylsiloxane units.

According to DE-A 37 16 372, organopolysiloxanes containing Si-bonded hydrogen atoms and from 3 to 5 silicon atoms per molecule, comprising $[H(CH_3)_2Si]_2O$ and trialkoxysilanes, are prepared in a hydrolytic process.

BRIEF SUMMARY OF THE INVENTION

The object of the present invention is to provide organosilicon compounds which have Si-bonded hydrogen atoms and can be crosslinked rapidly with organosilicon compounds having radical containing aliphatic carbon-carbon multiple bonds in the presence of catalysts which promote the addition of Si-bonded hydrogen onto aliphatic multiple bond, achieving higher crosslinking rates than before. A further object is to provide crosslinkable compositions suitable for producing coatings which repel tacky substances. These objects are achieved by the invention.

DETAILED DESCRIPTION OF THE INVENTION

The present invention provides crosslinkable compositions comprising, (A) an organosilicon compound having radicals containing aliphatic carbon-carbon multiple bonds, (B) an organosilicon compound having Si-bonded hydrogen atoms, (C) a catalyst which promotes the addition of Si-bonded hydrogen onto aliphatic multiple bond, and optionally, (D) an agent which retards the addition of Si-bonded hydrogen onto aliphatic multiple bond at room temperature, wherein at least one (B) organosilicon compound having Si-bonded hydrogen atoms that are used are organosilicon compounds ($B^1$) comprising (a) terminal units of the formula $$H_aR_{3-a}SiO_{1/2} \quad (I)$$

and, optionally, terminal units of the formula $$R_3SiO_{1/2} \quad (I')$$

in which
R is identical or different and is a monovalent, optionally halogenated hydrocarbon radical having 1 to 8 carbon atoms per radical and is free from aliphatic multiple bonds, and
a is 1, 2 or 3,
with the proviso that at least 50 mole % of the terminal units are those of formula (I), (b) carbo-structural units G (II)
in which
G is identical or different and is a divalent to decavalent aliphatic hydrocarbon radical having 2 to 30 carbon atoms per radical optionally containing one or more heteroatoms selected from the group consisting of oxygen, boron, silicon, tin and titanium, with the proviso that at least two Si atoms are connected to one another via G, (c) units of the formulae

or

or mixtures thereof, in which
R is as defined above, and
b is 0, 1 or 2,
with the provisos that b in formula (III') is not 2 and the units of formula (III) or (III') are connected via the Si atoms to the carbo-structural units G, and, optionally, (d) units of the formula

in which
R is as defined above,
c is 0 or 1 and
d is 1 or 2 and the sum c+d is 1 or 2,
with the proviso that the units of formula (IV) are located between the units of formula (III) or (III') and the terminal units of the formula (I) or (I'), and with the proviso that the organosilicon compounds ($B^1$) on average contain at least 4 Si-bonded hydrogen atoms per molecule. For purposes of the present invention, it is understood that each of the components (A)–(D) may be a single compound or mixture of compounds.

The present invention additionally provides crosslinkable compositions wherein at least some of the (B) organosilicon compounds having Si-bonded hydrogen atoms used are organosilicon compounds ($B^1$) which can be prepared by in a first step,
reacting aliphatic hydrocarbon compounds (1) having aliphatic multiple bonds and 2 to 30 carbon atoms, optionally containing one or more heteroatoms selected from the group consisting of oxygen, boron, silicon, tin and titanium, with silanes (2) of the formula $$H R_b SiX_{3-b}$$

in which

R and b are as defined above and

X is identical or different and is a halogen atom or a radical of the formula —$OR^1$ in which $R^1$ is an alkyl radical having 1 to 8 carbon atoms per radical, which is optionally substituted by an ether oxygen atom, in the presence of catalysts (3) which promote the addition of Si-bonded hydrogen onto aliphatic multiple bond, and removing excess silanes (2) by distillation, the ratio used of Si-bonded hydrogen in silane (2) to aliphatic double bond in hydrocarbon compound (1) being from 1.0 to 2.0, and to aliphatic triple bond in hydrocarbon compound (1) being from 2.0 to 4.0, in a second step, reacting the compounds of step one containing hydrolyzable groups, with silanes (4) of the formula $$H_aR_{3-a}SiZ$$

or siloxanes (5) of the formula $$H_aR_{3-a}SiOSiR_{3-a}H_a$$

in which

R and a are as defined above and

Z is a halogen atom or a radical of the formula —$OR^2$ in which $R^2$ is a monovalent hydrocarbon radical having 1 to 8 carbon atoms per radical, which is optionally substituted by an ether oxygen atom, and water in the presence of catalysts (6) which promote hydrolysis, the ratio used of Si atoms in silanes (4) or siloxanes (5) to hydrolyzable groups in the compounds obtained from the first step being from 0.8 to 5.0, and, optionally, in a third step, equilibrating the resulting organosilicon compounds ($B^1$) having Si-bonded hydrogen atoms with organopolysiloxanes (7) which may contain Si-bonded hydrogen atoms and which are selected from the group consisting of linear organopolysiloxanes containing terminal triorganosiloxy groups, linear organopolysiloxanes containing terminal hydroxyl groups, branched organopolysiloxanes optionally containing hydroxyl groups, cyclic organopolysiloxanes, and copolymers comprising diorganosiloxane and monoorganosiloxane units, with the proviso that the organosilicon compounds ($B^1$) thus obtained, having Si-bonded hydrogen atoms, possess on average at least 4 Si-bonded hydrogen atoms per molecule.

The invention further provides, organosilicon compounds ($B^1$) having Si-bonded hydrogen atoms and comprising (a) terminal units of the formula $$H_aR_{3-a}SiO_{1/2} \quad (I),$$

and, optionally units of the formula $$R_3SiO_{1/2} \quad (I')$$

in which

R and a are as defined above with the proviso that at least 50 mole % of the terminal units are those of formula (I), (b) carbo-structural units G (II)

in which

G is identical or different and is a divalent to decavalent aliphatic hydrocarbon radical having 2 to 30 carbon atoms per radical which may contain one or more heteroatoms selected from the group consisting of oxygen, boron, silicon, tin and titanium, with the proviso that at least two Si atoms are connected to one another via G, (c) units of the formulae $$R_bSiO_{\frac{3-b}{2}} \quad (III),$$

or $$R_bSiO_{\frac{2-b}{2}} \quad (III')$$

in which

R and b are as defined above, with the proviso that the units of formula (III) or (III') are connected via the Si atoms to the carbo-structural units G, and optionally, (d) units of the formula $$H_cR_dSiO_{\frac{4-c-d}{2}} \quad (IV)$$

in which

R, c and d are as defined above, with the proviso that the units of formula (IV) are located between the units of formula (II) or (III') and the terminal units of formula (I) or (I') and with the proviso that the organosilicon compounds ($B^1$) having Si-bonded hydrogen atoms on average contain at least 4 Si-bonded hydrogen atoms per molecule.

The invention further provides a process for preparing the organosilicon compounds ($B^1$) having Si-bonded hydrogen atoms, which comprises in a first step, reacting aliphatic hydrocarbon compounds (1) having aliphatic multiple bonds and 2 to 30 carbon atoms, and which may contain in each case one or more heteroatoms selected from the group consisting of oxygen, boron, silicon, tin and titanium, with silanes (2) of the formula $$HR_bSiX_{3-b}$$

in which

R, X and b are as defined above, in the presence of catalysts (3) which promote the addition of Si-bonded hydrogen onto aliphatic multiple bond, and removing excess silanes (2) by distillation, the ratio used of Si-bonded hydrogen in silane (2) to aliphatic double bond in hydrocarbon compound (1) being from 1.0 to 2.0, and to aliphatic triple bond in hydrocarbon compound (1) being from 2.0 to 4.0, in a second step, reacting the resulting compounds, containing hydrolyzable groups, with silanes (4) of the formula $$H_aR_{3-a}SiZ$$

or siloxanes (5) of the formula $$H_aR_{3-a}SiOSiR_{3-a}H_a$$

in which

R, Z and a are as defined above, and water in the presence of catalysts (6) which promote hydrolysis, the ratio used of Si atoms in silanes (4) or siloxanes (5) to hydrolyzable groups in the compounds obtained from the first step being from 0.8 to 5.0, and, optionally, in a third step, equilibrating the resulting organosilicon compounds ($B_1$) having Si-bonded hydrogen atoms with organopolysiloxanes (7) which may contain Si-bonded hydrogen atoms and which are selected from the group consisting of linear organopolysiloxanes containing terminal triorganosiloxy groups, linear organopolysiloxanes containing terminal hydroxyl groups, branched organopolysiloxanes optionally containing hydroxyl groups, cyclic organopolysiloxanes, and copolymers comprising diorganosiloxane and monoorganosiloxane units, with the proviso that the organosilicon compounds ($B^1$) thus obtained, having Si-bonded hydrogen atoms, possess on average at least 4 Si-bonded hydrogen atoms per molecule.

An essential feature of the novel organosilicon compounds ($B^1$), containing Si-bonded hydrogen atoms, is that the total number of terminal Si-bonded hydrogen atoms per molecule, i.e. the Si-bonded hydrogen atoms present in the terminal units of formula (I), is greater than the total number per molecule of all Si atoms which are connected to one another via the carbo-structural unit G.

The novel organosilicon compounds ($B^1$) having Si-bonded hydrogen atoms exhibit good solubility in the above described constituent (A) of the crosslinkable composition.

The novel organosilicon compounds ($B^1$) having Si-bonded hydrogen atoms possess a viscosity of from 4 to 500 $mm^2.s^{-1}$ at 25° C., preferably from 4 to 100 $mm^2.s^{-1}$ at 25° C. and more preferably from 4 to 40 $mm^2.s^{-1}$ at 25° C.

The novel organosilicon compounds ($B^1$) having Si-bonded hydrogen atoms include, on average per molecule, from 4 to 50 Si-bonded hydrogen atoms, preferably from 6 to 30 Si-bonded hydrogen atoms, more preferably from 8 to 25 Si-bonded hydrogen atoms.

The novel organosilicon compounds ($B^1$) having Si-bonded hydrogen atoms possess a hydrogen equivalent weight of from 60 to 300 g per mole of Si-bonded hydrogen, preferably from 90 to 150 g per mole of Si-bonded hydrogen.

The radical R in the organosilicon compounds ($B^1$) having Si-bonded hydrogen atoms is free from aliphatic multiple bonds, so that there is no autocrosslinking leading to instances of insolubility.

Examples of radicals R are alkyl radicals, such as the methyl, ethyl, n-propyl, isopropyl, 1-n-butyl, 2-n-butyl, isobutyl, tert-butyl, n-pentyl, isopentyl, neopentyl, tert-pentyl radical; hexyl radicals, such as the n-hexyl radical; heptyl radicals, such as the n-heptyl radical; octyl radicals, such as the n-octyl radical and isooctyl radicals, such as the 2,2,4-trimethylpentyl radical; cycloalkyl radicals, such as cyclopentyl, cyclohexyl, cycloheptyl radicals and methylcyclohexyl radicals; aryl radicals, such as the phenyl radical; alkaryl radicals, such as o-, m-, p-tolyl radicals, xylyl radicals and ethylphenyl radicals and aralkyl radicals, such as the benzyl radical, the α- and β-phenylethyl radical. The methyl radical is preferred.

Examples of halogenated radicals R are haloalkyl radicals, such as the 3,3,3-trifluoro-n-propyl radical, the 2,2,2',2',2'-hexafluoroisopropyl radical, the heptafluoroisopropyl radical, and haloaryl radicals, such as the o-, m- and p-chlorophenyl radical.

Examples of alkyl radicals $R^1$ are the methyl, ethyl, n-propyl, isopropyl, 1-n-butyl, 2-n-butyl, iso-butyl and tert-butyl radical. The methyl and ethyl radical are preferred. Examples of alkyl radicals $R^1$ which are substituted by an ether oxygen atom are the methoxyethyl and ethoxyethyl radical.

Examples of hydrocarbon radicals $R^2$ are alkyl radicals, such as the methyl, ethyl, n-propyl, isopropyl, 1-n-butyl, 2-n-butyl, isobutyl, and tert-butyl radical, the methyl and ethyl radical being preferred, and the radical of the formula $-C(=CH_2)CH_3$. Examples of alkyl radicals $R^2$ which are substituted by an ether oxygen atom are the methoxyethyl and ethoxyethyl radical.

A preferred example of the halogen atom X is the chlorine atom.

Examples of radicals Z are $-Cl$, $-Br$, $-OCH_3$, $-OC_2H_5$ and $-OC(=CH_2)CH_3$.

a is 1 or 2, preferably 1.

b is 0 or 1, preferably 0.

c is 0.

The sum of c+d is preferably 2.

An example of the terminal unit of formula (I) is the hydridodimethylsiloxane unit.

The carbo-structural unit G is a divalent to decavalent, aliphatically saturated hydrocarbon radical, preferably a trivalent to decavalent, aliphatically saturated hydrocarbon radical.

As carbo-structural unit G it is preferred to use radicals of the formula $$R^4(CR^3H-CH_2-)_x \qquad (II)$$

in which $R^4$ is a divalent to decavalent, aliphatically saturated hydrocarbon radical having 1 to 10 carbon atoms, which may contain one or more heteroatoms selected from the group consisting of oxygen, boron, silicon, tin and titanium, $R^3$ is a hydrogen atom or an alkyl radical having 1 to 6 carbon atoms per radical, and x is 2, 3, 4, 5, 6, 7, 8, 9 or 10, preferably 3, 4, 5 and 6, more preferably 3.

Examples of alkyl radicals $R^3$ are the methyl, ethyl, n-propyl, isopropyl, 1-n-butyl, 2-n-butyl, isobutyl, tert-butyl, n-pentyl, isopentyl, neopentyl, tert-pentyl radical and hexyl radicals, such as the n-hexyl radical. Preference is given to $R^3$ as a hydrogen atom.

Examples of divalent carbo-structural units G are those of the formulae $-CH_2CH_2-$, $-CH_2CH_2CH_2CH_2-$, $-(CH_2)_6-$, $-(CH_2)_{10}-$, $-(CH_2)_3O(CH_2)_3-$, $-CH_2CH_2-C_6H_4-CH_2CH_2-$ and $-CH_2CH_2Si(CH_3)_2CH_2CH_2-$.

Examples of trivalent carbo-structural units G are those of the formulae $(-CH_2CH_2)_3C_6H_9$, $(-CH_2CH_2)_3C_6H_3$, $(-CH_2CH_2CH_2OCH_2)_3C-CH_2CH_3$, $(-CH_2CH_2CH_2)_3B$, $(-CH_2CH_2)_3SiCH_3$ and $(-CH_2CH_2)_3SnC_4H_9$.

Examples of tetravalent carbo-structural units G are those of the formulae $(-CH_2CH_2)_4C_4H_4$, $(-CH_2CH_2)_4Sn$, $(-CH_2CH_2)_4Ri$, (—$CH_2CH_2CH_2O$)$_2$CH—CH(O$CH_2CH_2CH_2$—)$_2$ and

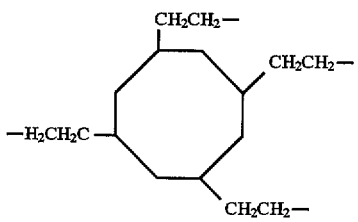

Carbo-structural units G of higher valency may be those of the formula (—$CH_2CH_2$)$_3$Si$CH_2CH_2$Si($CH_2CH_2$—)$_3$ or saturated oligomers of dienes such as butadiene or isoprene.

Carbo-structural units G are those having a valency of 3, 4, 5 and 6, with trivalent carbo-structural units being preferred.

Organosilicon compounds (B$^1$) having Si-bonded hydrogen atoms are those consisting of units of formula (I), G and (III).

Examples of organosilicon compounds (B$^1$) having Si-bonded hydrogen atoms are those of the formula

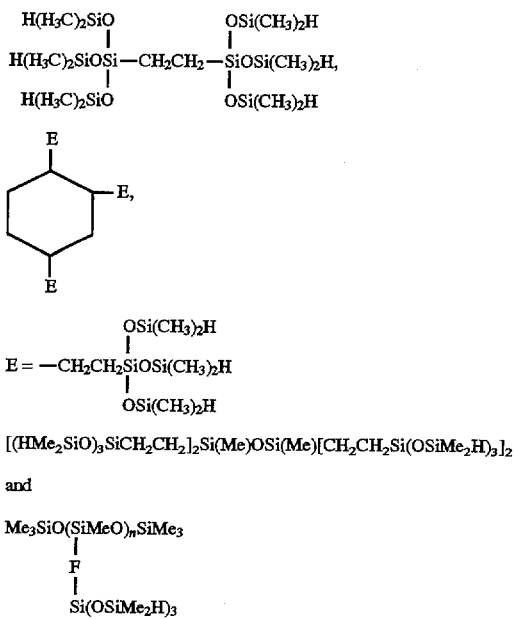

Me=methyl radical
n=3–30
F=—$CH_2CH_2$—

The hydrocarbon compounds (1) used in the first step of the novel process include from two to ten aliphatic double bonds or an aliphatic triple bond, preferably from three to six aliphatic double bonds, more preferably three aliphatic double bonds.

As hydrocarbon compounds (1) it is preferred to use those of the formula $R^4(CR^3=CH_2)_x$ in which $R^4$, $R^3$ and x are as defined above.

Examples of hydrocarbon compound (1) are acetylene, 1,5-hexadiene, 1,9-decadiene, diallyl ether, divinylbenzene, divinyldimethylsilane, 1,2,4-trivinylcyclohexane, 1,3,5-trivinylcyclohexane, 1,3,5-trivinylbenzene, triallylboron, trimethylolpropane triallyl ether, trivinylmethylsilane, trivinylbutyltin, tetravinylcyclobutane, tetravinylidenecyclobutane, tetravinyltitanium, 1,1,2,2-tetraallyloxyethane, cyclooctatetraene, 1,3,5,7-tetravinylcyclooctane, 1,2-bis(trivinylsilyl)ethane, oligobutadiene and oligoisoprene.

Examples of silanes (2), which are used in the first step of the novel process, are
$HSiCl_3$,
$HSiBr_3$,
$HSi(OMe)_3$,
$HSi(OEt)_3$,
$HMeSiCl_2$,
$HMeSi(OMe)_2$ and
$H_2SiCl_2$.

Preferred silanes (2) are $HSiCl_3$ and $H(CH_3)SiCl_2$, with $HSiCl_3$ being more preferred.

In the first step of the novel process it is possible to use one kind of hydrocarbon compound (1) or different kinds of hydrocarbon compounds (1).

In the first step of the novel process it is possible to use one kind of silane (2) or different kinds of silane (2).

In the first step of the novel process, the ratio of Si-bonded hydrogen in silane (2) to aliphatic double bond in the hydrocarbon compound (1) is from 1.0 to 2.0, preferably from 1.0 to 1.5, more preferably from 1.0 to 1.2, and the ratio of Si-bonded hydrogen in silane (2) to aliphatic triple bond in the hydrocarbon compound (1) is from 2.0 to 4.0, preferably from 2.0 to 3.0, more preferably from 2.0 to 2.4.

As catalysts (3) which promote the addition of Si-bonded hydrogen onto aliphatic double bond it is also possible in the novel process to use the same catalysts which has been used to date for promoting the addition of Si-bonded hydrogen onto aliphatic multiple bond. The catalysts (3) comprise a metal from the group of the platinum metals or a compound or a complex from the group of the platinum metals. Examples of such catalysts are metallic and finely divided platinum, possibly on supports such as silica, alumina or activated carbon, compounds or complexes of platinum, such as platinum halides, e.g. $PtCl_4$, $H_2PtCl_6.6H_2O$, $Na_2PtCl_4.4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6.6H_2O$ and cyclohexanone, platinum-vinylsiloxane complexes, such as platinum-1,3-divinyl-1,1,3,3-tetramethyldisiloxane complexes with or without a content of detectable, inorganically bonded halogen, bis(gammapicoline)-platinum dichloride, trimethylenedipyridineplatinum dichloride, dicyclopentadieneplatinum dichloride, dimethyl sulfoxideethyleneplatinum(II) dichloride, cyclooctadiene-platinum dichloride, norbornadiene-platinum dichloride, gamma-picoline-platinum dichloride, cyclopentadiene-platinum dichloride, and reaction products of platinum tetrachloride with olefin and primary amine or with secondary amine or primary and secondary amine, in accordance with U.S. Pat. No. 4,292,434, such as the reaction product of platinum tetrachloride, as a solution in 1-octene, with sec-butylamine, or ammonium-platinum complexes in accordance with EP-B 110 370.

In the first step of the process the catalyst (3) is used in quantities of from 1 to 50 ppm by weight (parts by weight per million parts by weight), preferably in quantities of from 5 to 20 ppm by weight, in each case calculated as elemental platinum and based on the overall weight of hydrocarbon compound (1) and silane (2).

The first step of the process is carried out at the pressure of the surrounding atmosphere, i.e. at about 1020 hPa (abs.), but can also be carried out at higher or lower pressures. The first step of the process is carried out at a temperature of from 20° C. to 150° C., preferably from 40° C. to 120° C., more preferably from 60° C. to 120° C.

In the first step of the process it is possible to use inert organic solvents, although the use of inert organic solvents is not preferred. Examples of inert organic solvents are toluene, xylene, octane isomers, butyl acetate, 1,2-dimethoxyethane, tetrahydrofuran and cyclohexane.

The inert organic solvents used optionally are removed by distillation following the first step of the process.

It is within the scope of the present invention to use, in the first step of the process, in place of the hydrocarbon compound (1) in combination with the s/lane (2), incompletely reacted intermediates from the reaction of (1) with (2), i.e. intermediates which still have aliphatically unsaturated double bonds, and to react them further with s/lane (2) to give the end product of the first step of the process.

An example is the reaction of acetylene with $HSiCl_3$ to give $Cl_3SiCH_2CH_2SiCl_3$ in the first step of the process. An intermediate produced is $CH_2=CHSiCl_3$, which can be used as starting material in place of acetylene and, when reacted with $HSiCl_3$, leads to the same end product of the first step of the process, $Cl_3SiCH_2CH_2SiCl_3$.

Another example is the reaction of 1,5-hexadiene with $HSi(OEt)_3$ (Et=ethyl radical) to give $(OEt)_3Si(CH_2)_6Si(OEt)_3$ in the first step of the process. An intermediate produced is $CH_2=CH(CH_2)_4Si(OEt)_3$, which can be used as starting material in place of 1,5-hexadiene and, when reacted with $HSi(OEt)_3$ (Et=ethyl radical), leads to the same end product of the first step of the process, $(OEt)_3Si(CH_2)_6Si(OEt)_3$.

Another example is the reaction of 1,2,4-trivinylcyclohexane with $HSiCl_3$ to give

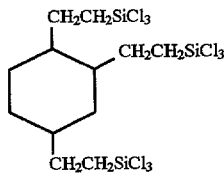

in the first step of the process.
An intermediate produced is

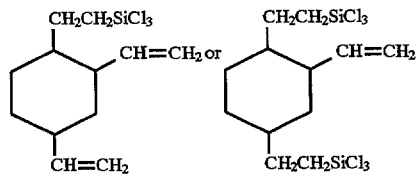

which can be used as starting material in place of 1,2,4-trivinylcyclohexane and, when reacted with $HSiCl_3$, leads to the same above mentioned and product of the first step of the process.

Examples of silanes (4) which are used in the second step of the novel process are dimethylchlorosilane, methychlorosilane, chlorosilane, methylbromosilane, dimethyknethoxysilane, methylmethoxysilane, dimethylethoxysilane, diethylchlorosilane, dimethylisopropenoxysilane, methyldiisopropenoxysilane.

Examples of siloxanes (5) which are used in the second step of the novel process are 1,1,3,3-tetramethyldisiloxane, 1,3-dimethyldisiloxane, 1,1,1,3,3-pentamethyldisiloxane, and 1,1-dimethyldisiloxane.

In the second step of the novel process it is possible to use one kind of silane (4) or different kinds of silane (4) and one kind of siloxane (5) or different kinds of siloxane (5).

The hydrolysis-promoting catalysts (6) used in the second step of the novel process may be the same as those which have been used to date to promote the hyrolysis of organosilicon compounds containing hydrolyzable groups. As catalyst (6) it is possible to use acids or bases, preferably acids. Examples of acids are hydrochloric, hydrobromic, sulfuric and perchloric acid, preferably hydrochloric acid. Hydrochloric acid in a concentration of from 1% to 20% is more preferred.

In the second step of the process, water is used in quantifies of from 20 to 200 g per mole of Si-bonded hydrolyzable group X.

In the second step of the novel process the ratio of Si atoms in silanes (4) or siloxanes (5) to hydrolyzable groups in the compounds containing hydrolyzable groups that are obtained from the first step of the process is from 0.8 to 5.0, preferably from 0.8 to 2.5, more preferably from 1.0 to 2.5.

Preferred procedures in the second step of the process are either the premixing of compounds obtained from the first step of the process with silanes (4) and conjoint cohydrolysis by metered addition of this mixture to an initial charge of acid, or the mixing of siloxanes (5) with acid and metered addition of the compounds obtained from the first step of the process.

The second step of the process is carried out at the pressure of the surrounding atmosphere, at approximately 1020 hPa (abs.), but can also be carried out at higher or lower pressures. Furthermore, the second step of the process is carried out at a temperature of from 0° C. to 40° C., preferably from 10° C. to 25° C.

Working up of the second step of the process is accomplished by separating off the aqueous phase and washing with water and bicarbonate solution.

Excess silane (4) and siloxane (5) are separated off following the second step of the process, preferably by distillative removal.

In the second step of the process it is possible also to use inert organic solvents. Examples of inert organic solvents are cyclohexane, toluene, xylenes and lower ketones, such as acetone or butanone.

The inert organic solvents used optionally are separated off after the second step of the process, preferably by distillative removal.

The organosilicon compounds containing Si-bonded hydrogen atoms that are obtained after the second step of the process can be equilibrated, in a third step of the process, with organosiloxanes (7) which may or may not contain Si-bonded hydrogen atoms. If equilibration is carried out, the novel organosilicon compounds, containing Si-bonded hydrogen atoms, preferably include not more than ten units of the formula (IV), more preferably not more than five units of formula (W).

As organopolysiloxanes (7) which may or may not contain Si-bonded hydrogen atoms, use is made of those selected from the group consisting of linear organopolysiloxanes, containing terminal triorganosiloxy groups, of the formula $R_3'SiO(SiR_2'O)_rSiR_3'$,
in which
R' is as defined for R or is a hydrogen atom,
r is 0 or an integer from 1 to 500, preferably 10 to 200, linear organopolysiloxanes, containing terminal hydroxyl groups, of the formula $HO(SiR_2'O)_sH$,
in which
R' is as defined above and
s is an integer from 1 to 1000, preferably from 10 to 500, branched organopolysiloxanes, with or without hydroxyl groups and comprising units of the formula $R_3'SiO_{1/2}$, $R_2'SiO$ and $R'SiO_{3/2}$, in which
R' is as defined above, cyclic organopolysiloxanes of the formula $(R_2'SiO)_t$,
in which
R' is as defined above and
t is an integer from 3 to 12,
and copolymers comprising units of the formula $R_2'SiO$ and $R'SiO_{3/2}$, in which
R' is as defined above.

Preferred organopolysiloxanes (7) are those of the formulae $R_3'SiO(SiR_2'O)_rSiR_3'$ and $HO(SiR_2'O)_sH$.

The quantitative ratio of the organopolysiloxanes (7) used in the course of the optional equilibration to the organosilicon compounds having Si-bonded hydrogen atoms is governed merely by the desired proportion of Si-bonded hydrogen atoms in the organosilicon compounds produced in the course of the optional equilibration, and by the desired average chain length.

In the optional equilibration, use is made of acidic catalysts which promote the equilibration.

Examples of acidic catalysts are sulfuric acid, phosphoric acid, trifluoromethanoic acid, phosphorus nitride chlorides and acidic catalysts which are solid under the reaction conditions, such as acid-activated bleaching earth, acidic zeolites, sulfonated charcoal and sulfonated styrene-divinylbenzene copolymer. Phosphorus nitride chlorides are preferred. Phosphorus nitride chlorides are used in quantities of from 5 to 1000 ppm by weight (=parts per million), especially from 50 to 200 ppm by weight, based in each case on the overall weight of the organosilicon compounds and organopolysiloxanes (7) used.

The optional equilibration is carried out at from 100° C. to 150° C. and at the pressure of the surrounding atmosphere, at about 1020 hPa (abs.). Optionally, it is possible to apply higher or lower pressures. Equilibration is preferably carried out in from 5% to 20% by weight, based on the overall weight of the organosilicon compounds and organopolysiloxanes (7) used in each case, of water-immiscible solvent, such as toluene. Before working up the mixture obtained in the course of equilibration, the catalyst can be rendered inactive.

The novel process can be carried out batchwise, semicontinuously or continuously.

The crosslinkable compositions comprising the novel organosilicon compounds ($B^1$) which contain Si-bonded hydrogen atoms are used to produce coatings which repel tacky substances, for example for producing release papers.

The self-adhesive materials which are joined to the release paper are prepared by the off-line technique or the in-line technique. In the off-line technique, the silicone composition is applied to the paper and crosslinked and then, in a subsequent stage, usually after the release paper has been wound up onto a roll and after the roll has been stored, an adhesive film, which lies, for example, on a label face paper, is applied to the coated paper and then the assembly is compressed. In the in-line technique, the silicone composition is applied to the paper and crosslinked, the silicone coating is coated with the adhesive, the label face paper is then applied to the adhesive, and finally the assembly is compressed.

As constituent (A) of the novel compositions it is also possible to use the same organosilicon compounds, containing aliphatic carbon-carbon multiple bonds, which have been used in all crosslinkable compositions known to date comprising organosilicon compounds containing aliphatic carbon-carbon multiple bonds, organosilicon compounds containing Si-bonded hydrogen atoms, and catalysts which promote the addition of Si-bonded hydrogen onto aliphatic multiple bond.

In the case of the novel compositions it is possible to use one kind of constituent (A) or different kinds of constituent (A).

As organosilicon compounds (A) which contain radicals having aliphatic carbon-carbon multiple bonds, use is made of linear or branched organopolysiloxanes comprising units of the formula

 (V)

in which
$R^5$ is a monovalent hydrocarbon radical that has 1 to 18 carbon atoms per radical and is free from aliphatic carbon-carbon multiple bonds, and
$R^6$ is a monovalent hydrocarbon radical containing at least one terminal aliphatic carbon-carbon multiple bond and having 2 to 12 carbon atoms per radical,
e is 0, 1, 2 or 3,
f is 0, 1 or 2
and the sum e+f is 0, 1, 2 or 3,
with the proviso that on average there is at least one radical $R^6$ per molecule, preferably at least 2 radicals $R^6$ per molecule.

Preferred organosilicon compounds (A) are organopolysiloxanes of the formula

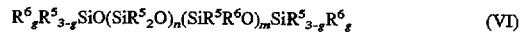 (VI)

in which
$R^5$ and $R^6$ are as defined above,
g is 0, 1 or 2,
n is 0 or an integer from 1 to 1500 and
m is 0 or an integer from 1 to 200,
with the proviso that there is at least one radical $R^6$ per molecule, in particular at least 2 radicals $R^6$ per molecule.

In formula (VI) the n units —$(SiR^5_2O)$— and m units —$(SiR^5R^6O)$— can be distributed in the organopolysiloxane molecule in any desired manner.

As organosilicon compounds (A) it is possible to use siloxane copolymers containing alkenyl groups, which are described in U.S. Pat. No. 5,241,034 and consist of siloxane blocks and hydrocarbon blocks. The alkenyl-containing siloxane copolymers described in U.S. Pat. No. 5,241,034 therefore belong to the disclosure content of the application.

As organosilicon compounds (A) it is possible to use organopolysiloxanes containing aliphatically unsaturated hydrocarbon radicals, as described in Applicant's German Patent Application 196 27 022.7. The organopolysiloxanes described in 196 27 022.7 contain fictional (T) and/or tetrafunctional (Q) units with unsaturated hydrocarbon radicals. Therefore, the organopolysiloxanes described in 196 27 022.7 belong to the disclosure content of the application.

The organosilicon compounds (A) have an average viscosity of from 100 to 100,000 mPa.s at 25° C., preferably from 100 to 10,000 mPa.s at 25° C., more preferably from 100 to 500 mPa-s at 25° C.

Examples of hydrocarbon radicals $R^5$ are alkyl radicals, such as the methyl, ethyl, n-propyl, isopropyl, n-butyl, isobutyl, tert-butyl, n-pentyl, isopentyl, neopentyl, tert-pentyl radical; hexyl radicals, such as the n-hexyl radical; heptyl radicals, such as the n-heptyl radical; octyl radicals, such as the n-octyl radical and isooctyl radicals, such as the 2,2,4-trimethylpentyl radical; nonyl radicals, such as the n-nonyl radical, decyl radicals, such as the n-decyl radical, dodecyl radicals, such as the n-dodecyl radical, octadecyl radicals, such as the n-octadecyl radical; cycloalkyl radicals, such as cyclopentyl, cyclohexyl, cycloheptyl radicals and methylcyclohexyl radicals; aryl radicals, such as the phenyl, naphtyl, anthryl and phenanthryl radical; alkaryl radicals, such as o-, m; p-tolyl radicals, xylyl radicals and ethylphenyl radicals; and aralkyl radicals, such as the benzyl radical, the α- and the β-phenylethyl radical.

Examples of radicals $R^6$ are alkenyl radicals, such as the vinyl, 5-hexenyl, 2,4-divinylcyclohexylethyl, 3,4-divinylcyclohexylethyl, 2-propenyl, 3-butenyl and 4-pentenyl radical; and alkynyl radicals, such as the ethynyl and 2-propynyl radical.

The novel organosilicon compounds ($B^1$) having Si-bonded hydrogen atoms may in the known crosslinkable compositions comprising (A) organosilicon compounds containing radicals having aliphatic carbon-carbon multiple bonds,
(B) organosilicon compounds having Si-bonded hydrogen atoms, and
(C) catalysts which promote the addition of Si-bonded hydrogen onto aliphatic multiple bond, replace some or all of the organosilicon compounds (B) having Si-bonded hydrogen atoms.

Where relatively long processing times (pot lives) are desired, the novel crosslinkable compositions may also comprise, as constituent (B), in addition to the novel organosilicon compounds ($B^1$), other known organosilicon compounds ($B^2$) having Si-bonded hydrogen atoms.

As organosilicon compound ($B^2$) having Si-bonded hydrogen atoms it is possible to use organopolysiloxanes comprising units of the formula

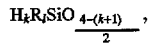

in which
R is as defined above,
k is 0 or 1,
l is 0, 1, 2 or 3 and
the sum k+l is not more than 3, preferably those of the formula

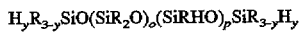

in which
R is as defined above,
y is 0 or 1,
o is 0 or an integer from 1 to 100 and
p is 0 or an integer from 1 to 100.

Examples of such organopolysiloxanes are copolymers comprising dimethylhydridosiloxane, methylhydridosiloxane, dimethylsiloxane and trimethylsiloxane units, copolymers comprising trimethylsiloxane, dimethylhydridosiloxane and methylhydridosiloxane units, copolymers comprising trimethylsiloxane, dimethylsiloxane and methylhydridosiloxane units, copolymers comprising methylhydridosiloxane and trimethylsiloxane units, copolymers comprising methylhydridosiloxane, diphenylsiloxane and trimethylsiloxane units, copolymers comprising methylhydridosiloxane, dimethylhydridosiloxane and diphenylsiloxane units, copolymers comprising methylhydridosiloxane, phenylmethylsiloxane, trimethylsiloxane and/or dimethylhydridosiloxane units, copolymers comprising methylhydridosiloxane, dimethylsiloxane, diphenylsiloxane, trimethylsiloxane and/or dimethylhydridosiloxane units, and copolymers comprising dimethylhydridosiloxane, trimethylsiloxane, phenylhydridosiloxane, dimethylsiloxane and/or phenylmethylsiloxane units.

Relatively long pot lives coupled with a high crosslinking rate are obtained when the novel organosilicon compound ($B^1$) is used in quantities where the amount of Si-bonded hydrogen is not more than 50% by weight, preferably 20%–50% by weight, more preferably 30%–40% by weight, based on the overall weight of the Si-bonded hydrogen atoms in the organosilicon compounds ($B^1$) and ($B^2$) used.

Constituent (B) is used in quantities of from 0.8 to 5.0, preferably from 0.8 to 2.5, more preferably from 1.0 to 2.0, gram-atoms of Si-bonded hydrogen per mole of Si-bonded radical containing aliphatic carbon-carbon multiple bond in the constituent (A).

In the novel compositions, it is also possible to use as catalyst (C), which promotes the addition of Si-bonded hydrogen onto aliphatic double bond, the same catalysts which have been used to promote crosslinking, in the compositions known to date for the crosslinking of organosilicon compounds containing aliphatic multiple bonds with compounds containing Si-bonded hydrogen. As constituent (C) it is preferred to use the above mentioned catalysts (3).

Catalyst (C) is used in quantities of from 5 to 500 ppm by weight (parts by weight per million parts by weight), in particular from 10 to 200 ppm by weight, calculated as elemental platinum metal and based on the overall weight of the organosilicon compounds (A) and (B).

Examples of further constituents which can be used in the novel compositions are agents which retard the addition of Si-bonded hydrogen onto aliphatic multiple bond at room temperature, so-called inhibitors (D), agents for establishing the release force, solvents, adhesion promoters and pigments.

As inhibitors (D) it is possible with the novel compositions to use all inhibitors which have been used to date for the same purpose. Examples of inhibitors are 1,3-divinyl-1,1,3,3-tetramethyldisiloxane, benzotriazole, dialkylformamides, alkylthioureas, methyl ethyl ketoxime, organic or organosilicon compounds having a boiling point of at least 25° C. at 1012 mbar (abs.) and at least one aliphatic triple bond in accordance with U.S. Pat. No. 3,445,420, such as 1-ethynylcyclohexan-1-ol, 2-methyl-3-butyn-2-ol, 3-methyl-1-pentyn-3-ol, 2,5-dimethyl-3-hexyne-2,5-diol and 3,5-dimethyl-1-hexyn-3-ol, 3,7-dimethyloct-1-yn-6-en-3-ol, inhibitors in accordance with U.S. Pat. No. 2,476,166, such as a mixture of diallyl maleate and vinyl acetate, and inhibitors in accordance with U.S. Pat. No. 4,504,645, such as maleic monoesters, and inhibitors in accordance with the Applicant's German application 195 41 451.9, such as the compound of the formula HC≡C—C(CH$_3$)(OH)—CH$_2$—CH$_2$—CH═C(CH$_3$)$_2$, commercially available under the trade name "Dehydrolinalool" from BASF.

The inhibitor (D) is used in quantities of from 0.01% to 10% by weight, based on the overall weight of the organosilicon compounds (A) and (B).

Examples of agents for establishing the release force of the tacky-substance-repelling coatings produced using the novel compositions are silicone resins comprising units of the formula

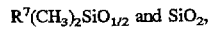

so-called MQ resins, in which $R^7$ is a hydrogen atom, a methyl radical, a vinyl radical or a radical A which is described in above-cited U.S. Pat. No. 5,241,034 and is hereby incorporated by reference, and where the units of the formula $R^7(CH_3)_2SiO_{1/2}$ can be identical or different. The ratio of units of the formula $R^7(CH_3)_2SiO_{1/2}$ to units of the formula $SiO_2$ is from 0.6 to 2. The silicone resins are used in quantities of from 5% to 80% by weight, based on the overall weight of the organosilicon compounds (A) and (B).

The solvents optionally used with the novel compositions can be the same solvents used with the compositions known to date comprising organopolysiloxanes having Si-bonded vinyl groups, organopolysiloxanes having Si-bonded hydrogen, and catalyst which promotes the addition of Si-bonded hydrogen onto aliphatic double bond. Examples of such solvents are petroleum spirits, for example alkane mixtures having a boiling range from 80° C. to 110° C. at 1012 mbar (abs.), n-heptane, benzene, toluene and xylenes, halogenated alkanes having 1 to 6 carbon atoms, such as methylene chloride, trichloroethylene and perchloroethylene, ethers, such as di-n-butyl ether, esters, such as ethyl acetate, and ketones, such as methyl ethyl ketone and cyclohexanone.

Where organic solvents are used, they are used in quantities of from 10% to 95% by weight, based on the weight of the organosilicon compounds (A).

When mixing the constituents (A), (B), (C) and, optionally, (D), the sequence is not critical; however, for practice it is appropriate to add the constituent (C), the catalyst, to the mixture of the other constituents last.

The crosslinking of the novel compositions takes place at from 50° C. to 150° C., preferably from 70° C. to 120° C. An advantage with the novel compositions is that rapid crosslinking is achieved even at low temperatures. As energy sources for the crosslinking by heating it is preferred to use ovens, for example convection ovens, heating tunnels, heated rolls, heated plates or heat rays in the infrared region.

Apart from heating, the novel compositions can also be crosslinked by irradiation with ultraviolet light or by irradiation with UV and IR light. The ultraviolet light used is that having a wavelength of 253.7 nm. In commerce there are a large number of lamps which emit ultraviolet light of a wavelength of 200 to 400 nm, and which preferentially emit ultraviolet light with a wavelength of 253.7 nm.

The application of the novel compositions to the surfaces which are to be made repellent to tacky substances can be accomplished in any desired manner which is suitable and known for the production of coatings from liquid substances, for example by dipping, spreading, pouring, spraying, rolling, printing by means of an offset gravure coating device, by knife-coating or by means of an airbrush.

The surfaces which are to be made repellent to tacky substances and can be treated in the context of the invention may comprise surfaces of any desired substances which are solid at room temperature and 1012 mbar (abs.). Examples of such surfaces are those of paper, wood, cork and plastics films, for example polyethylene films or polypropylene films, woven and nonwoven cloth of natural or synthetic fibers or glass fibers, ceramic articles, glass, metals, polyethylene-coated paper, and cards and boards, including those of asbestos. The above mentioned polyethylene may comprise high-pressure, medium-pressure or low-pressure polyethylene. The paper can comprise low-grade paper types, such as absorbent papers, including raw kraft paper, i.e. kraft paper which has not been pretreated with chemicals and/or polymeric natural substances, having a weight of from 60 to 150 g/m², unsized papers, papers of low freeness, mechanical papers, unglazed or uncalendered papers, papers which are smooth on one side owing to the use of a dry glazing cylinder during their production, without additional complex measures, and are therefore referred to as "machine-glazed papers", uncoated papers or papers produced from waste paper, i.e. so-called recycled papers. The paper to be treated in accordance with the invention may also comprise high-grade papers, such as low-absorbancy papers, sized papers, papers of high freeness, chemical papers, calendered or glazed papers, glassine papers, parchmentized papers or precoated papers. The cards and boards may be of low or high grade.

The novel compositions are suitable, for example, for the production of release, backing and interleaving papers, including interleaving and release papers which are used in the production of, cast films or decorative films, or of foams, including those of polyurethane. The novel compositions are also suitable for the production of release, backing and interleaving cards, films and cloths, for treating the reverse sides of self-adhesive tapes or self-adhesive films or the written faces of self-adhesive labels. The novel compositions are also suitable for treating packaging material such as paper, cardboard boxes, metal foils and drums, for example cardboard, plastic, wood or iron, which is intended for the storage and/or transportation of tacky goods, such as adhesives, sticky foodstuffs, for example cakes, honey, candies and meat, bitumen, asphalt, greased materials and crude rubber. A further example of the use of the novel compositions is the treatment of supports for the transfer of contact-adhesive layers in the so-called transfer process.

The novel compositions are suitable for the production of the self-adhesive materials connected to the release paper, both by the off-line technique and by the in-line technique.

EXAMPLE 1 a) Preparation of 1,2,4-tris [2-trichlorosilylethyl] cyclohexane

To 162 g of 1,2,4-trivinylcyclohexane there are added 4 mg of Pt in the form of a platinum-1,3-divinyl-1,1,3, 3-tetramethyldisiloxane complex, the so-called Karstedt catalyst, which corresponds to the catalyst as prepared in accordance with U.S. Pat. No. 3,775,452 (issued on Nov. 27, 1973, Bruce D. Karstedt, General Electric Co.), and the mixture is heated to about 80° C. A total of 450 g of trichlorosilane are added dropwise over a period of about 2 hours, the temperature of the liquid phase slowly rising under reflux and then falling again toward the end of the reaction. The batch is boiled at reflux for an additional 1 hour and the volatile constituents are distilled off up to 100° C. at 3 mPa.s. The title substance is obtained in virtually quantitative yield (564 g).

b) Preparation of the carbosiloxane crosslinking agent 1

167 g of 1,1,3,3-tetramethyldisiloxane are introduced together with 100 g of water and 20 g of conc. HCl at room temperature and the mixture is stirred with turbulence. While cooling the vessel, a solution of 71 g of 1,2,4-tris[2-trichlorosilylethyl]cyclohexane, whose preparation was described under a) above, in 24 g of cyclohexane is added dropwise, during which the internal temperature should not exceed 30° (2. The mixture is stirred for about 1 hour and then the aqueous phase is separated off, washed twice with 100 ml of water and then once with about 10% strength sodium carbonate solution. The reaction mixture is concentrated at 110° C. and 3 mPa-s, to give 90 g of a clear silicone oil having a viscosity of 31 mm/s. The $^{29}$Si-NMR spectrum shows a narrow peak group at −62 ppm for alkylsiloxy units and at −6 ppm for hydridodimethylsiloxy units, with an integral ratio of 1:2.87. The product has the structure of the formula

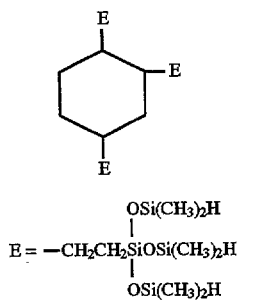

$$E = -CH_2CH_2SiOSi(CH_3)_2H$$
with OSi(CH₃)₂H groups above and below contains components of higher molecular mass and is free from Cl—Si compounds and 1,3,3-tetramethylsiloxane. It contains precisely 1.0 g-atom of Si-bonded hydrogen per 104 g.

EXAMPLE 2 a) Preparation of 1,2-bis(trichlorosilyl)ethane 162 g of vinyltrichlorosilane (obtained from the reaction of acetylene with trichlorosilane in the presence of the Karstedt catalyst) are heated to about 60° C. together with 4 mg of Pt in the form of the Karstedt catalyst which was described in Example 1 under a). A total of 150 g of trichlorosilane are metered in at a rate such that the reaction mixture remains permanently at reflux temperature. Toward the end of the reaction, the mixture is held by additional heating at boiling temperature for one hour more, and volatile constituents are distilled off in vacuo at about 50° C., leaving about 286 g of the title compound in combination with the 1,1 isomer. Over a period of time, the product crystallizes, and then has a melting point of about 40° C.

b) Preparation of the carbosiloxane crosslinking agent 2

The procedure of Example 1 under b) is repeated with the modification that, instead of 1,2,4-tris[2-trichlorosilylethyl]cyclohexane, a solution of 56 g of 1,2-bis[trichlorosilyl]ethane, whose preparation is described under a above), in 20 g of cyclohexane is added dropwise. The reaction temperature should be kept below 30° C.

After an additional reaction period at room temperature of one hour and following reductive concentration in vacuo, a thinly liquid silicone oil is obtained, having a viscosity of 4 mm²/s at 25° C., in about 85% of the theoretical yield. The integral ratio in the 29Si-NMR spectrum of alkylsiloxy to hydridodimethylsiloxy units is 1:2.9. The resulting carbosiloxane crosslinking agent has the structure of the formula

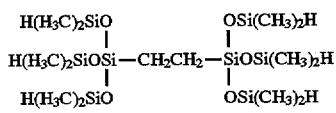

and contains precisely 1.0 g-atom of Si-bonded hydrogen per 90 g.

c) Preparation of the carbosiloxane crosslinking agent 3

The procedure of Example 2b is repeated with the modification that, instead of only 0.45 eq of chlorine per initially charged eq of Si-bonded hydrogen, exactly 1.0 eq of chlorine is metered in, in the form of a solution of 123 g of 1,2-bis[trichlorosilyl]ethane in about 40 g of cyclohexane. Identical implementation and workup give 180 g of a silicone oil having a viscosity of 4.5 mm²/s at 25° C. The integral ratio in the 29Si-NMR spectrum of alkylsiloxy to hydridodimethylsiloxy units is precisely 1:2.67. The resulting carbo siloxane crosslinking agent contains precisely 1.0 g-atom of Si-bonded hydrogen per 92 g.

EXAMPLE 3

100 g of an α,ω-divinyldimethylpolysiloxane containing 100 siloxane units (corresponding to 27 meq of C=C) are mixed with 0.30 g of the compound of the formula $HC≡C-C(CH_3)(OH)-CH_2-CH_2-CH=C(CH_3)_2$, which is commercially available from BASF under the trade name Dehydrolinalool, and with 5.4 g of the carbosiloxane crosslinking agent 1. 10.5 mg of Pt are added in the form of a solution of the Karstedt catalyst, described in Example 1 under a), in α,ω-divinyldimethylpolysiloxane, having a viscosity of 1000 mm²/s at 25° C. The H-Si/C=C ratio is 1.9. At temperatures which are constant, heat flux/time curves (DSC) of this mixture are recorded. The results are compiled in Table 1.

TABLE 1

| | | Reaction maximum | Reaction end | Total energy | Peak intensity* |
|---|---|---|---|---|---|
| Ex- | 80° C. | 23.6 sec. | 37.8 sec. | −30.9 J/g | 1500 mW/g · s |
| ample | 70° C. | 30.8 sec. | 44.4 sec. | −30.1 J/g | 700 mW/g · s |
| | 60° C. | 50.9 sec. | 73.8 sec. | −29.6 J/g | 150 mW/g · s |
| | 50° C. | 78.0 sec. | 125.4 sec. | −28.5 J/g | 30 mW/g · s |
| V1 | 80° C. | 995 sec. | 1200 sec. | −29.9 J/g | 5 mW/g · s |

*Peak height/peak width at half peak height (high value = high peak intensity)

Comparative Experiment 1 (V1)

The procedure of Example 3 is repeated with the modification that, instead of the carbosiloxane crosslinking agent 1, 3.3 g of a customary H-siloxane crosslinking agent is used, comprising about 40 hydridomethyl and 2 trimethylsilyl units. As in Example 3, the H-Si/C=C ratio is 1.9. The results of the DSC curves are compiled in Table 1.

Comparison shows that, although the ultimate conversion of the active C=C double bonds is virtually identical, the formulation containing the carbosiloxane crosslinking agent reaches the end of the reaction much faster. At 80° C., the peak intensity is 300 times as great. Even at 50° C., the reactivity is substantially higher than in the case of the conventional formulation at 80° C.

EXAMPLE 4

The formulation of Example 3 is reproduced with a reduced quantity of crosslinking agent, so that in each case only precisely 1.0 mol of SiH is used per mole of C=C double bonds of the vinyl polymer. The DSC curves were again recorded at temperatures which were constant in each case. The results are shown in Table 2.

TABLE 2

| | | Reaction maximum | Reaction end | Total energy | Peak intensity* |
|---|---|---|---|---|---|
| Example | 80° C. | 32.9 sec. | 59.4 sec. | −21.7 J/g | 370 mW/g · s |
| | 70° C. | 48.4 sec. | 100.8 sec. | −22.8 J/g | 180 mW/g · s |
| | 60° C. | 91.7 sec. | 192.0 sec. | −22.5 J/g | 36 mW/g · s |
| | 50° C. | 192.4 sec. | 292.8 sec. | −15.7 J/g | 8 mW/g · s |
| V2 | 80° C. | 1250 sec. | 1583 sec. | −15.2 J/g | 1.5 mW/g · s |

Comparative Experiment 2 (V2)

The formulation of Comparative Experiment 1 is reproduced with a reduced quantity of crosslinking agent, so that in each case only precisely 1.0 mol of SiH is used per mole of C=C double bond of the vinyl polymer. The results of the DSC curves are compiled in Table 2.

Owing to the lack of excess SiH, all formulations react more slowly than in Example 3. However, comparison at 80° C. again clearly shows the superiority of the carbosiloxane-crosslinked formulation in respect of rate and completeness of reaction.

EXAMPLE 5

100 g of the vinylsiloxane polymer from Example 3 are mixed homogeneously with 0.30 g of dehydrolinalool, and then 2.9 g of the carbosiloxane crosslinking agent 3 are stirred in. Finally, 5.2 mg of Pt are mixed in in the form of the Karstedt catalyst from Example 3. The formulation contains 50 ppm of Pt and has an HSi/C=C ratio of 1.2.

The freshly prepared mixtures are applied with a glass rod to satinized, low-absorbency glassine paper (67 g/ m²) and are subjected to a temperature of 120° C. for precisely 3 seconds or 5 seconds in a convection oven. During this exposure, the substrate reaches about 90° C. The results are compiled in Table 3.

TABLE 3

| | after 3 sec. | after 5 sec. |
|---|---|---|
| Example 5 | tack-free, definite mark | free from marks, no rub-off |
| Comparative Experiment 3 | liquid | not tack-free |

Comparative Experiment 3 (V3)

The procedure of Example 5 is repeated with the modification that, instead of the carbosiloxane crosslinking agent 3, 21 g of a customary H-siloxane crosslinking agent are used comprising about 40 hydridomethyl and 2 trimethylsilyl units (65 g contain 1.0 g-atom of Si-bonded hydrogen). As in Example 5, the H-Si/C=C ratio is 1.2. The results are compiled in Table 3.

EXAMPLE 6

The following formulations are prepared:

| | a | | b | | c | | d | | Comparative Experiment 4 | |
|---|---|---|---|---|---|---|---|---|---|---|
| | g | meq | g | meq | g | meq | g | meq | g | meq |
| α,Ω-Divinyl-PDMS | 40.00 | 10.80 | 40.00 | 10.80 | 40.00 | 10.80 | 40.00 | 10.80 | 40.00 | 10.80 |
| Dehydrolinalool | 0.09 | 0.60 | 0.09 | 0.60 | 0.09 | 0.60 | 0.09 | 0.60 | 0.09 | 0.60 |
| Carbosiloxane crosslinking agent 1 | 0.40 | 3.80 | 0.56 | 5.40 | 0.72 | 6.90 | 1.68 | 16.20 | — | — |
| Crosslinking agent $B^2$ | 0.81 | 12.40 | 0.70 | 10.80 | 0.60 | 9.30 | — | — | 1.05 | 16.20 |
| Platinum catalyst | 0.41 | | 0.41 | | 0.41 | | 0.41 | | 0.41 | |

The α,ω-divinyldimethylpolysiloxane (=α,ω-divinyl-PDMS) has an average chain length of about 100 Si atoms. Dehydrolinalool is obtainable from BASF and has a molecular weight of 152. Crosslinking agent $B^2$ is a polymer comprising hydridomethylsiloxy units with trimethylsilyl end groups and about 15.4 Si-H groups/kg. The platinum catalyst consists of Karstedt catalyst dissolved in α,ω-divinyldimethylpolysiloxane containing 10 g of Pt (calculated as Pt metal) per kg of catalyst solution.

In each formulation, the concentration of Si-bonded hydrogen is 1.5 times that of the C=C double bond. After application to supercalendered paper in a layer thickness of about 4 μm, all formulations are cured at 70° C. in a convection oven or at 80° C. (isothermally) and a DSC (Differential Scanning Calorimetry) spectrum is recorded.

| | | a | b | c | d | Comparative Experiment 4 |
|---|---|---|---|---|---|---|
| Curing at 90° C.: (time in sec.) | mark-free | 9 | 5 | 10 | 5 | >20 |
| | abrasion-resistant | 9 | 4 | 10 | 4 | 20 |
| DSC peak after seconds | | 300 | 246 | 342 | 24 | >1200 |
| gel time (25° C.) | | >76 h | 76 h | >76 h | <1 h | >76 h |

Formulation d) exhibits very good curing conditions, with a gel time of <1 h. Equal polymerization quality is achieved with formulation b), with a gel time of more than 3 days.

The exclusive use of crosslinking component $B^2$ (Comparative Experiment 4), on the other hand, leads to comparatively slow curing.

EXAMPLE 7

The formulations of Example 6b) and the comparative formulation 4 are prepared by replacing the 90 mg of dehydrolinalool with 70 mg of 1-ethynylcyclohexanol. The mixtures, about 50-fold, are tested in comparison on a coating machine. The length of the drying oven is 4.5 m. The circulating-air temperature is 150° C. The paper which is coated is supercalendered "Rhiliner 12" paper (from Rhinelander/USA) in a layer thickness of about 0.9 min. Immediately after curing, the non-crosslinked (extractable) fractions are determined by extraction over several days with MIBK (=methyl iso-butyl ketone) and are correlated with the respective belt speed.

| | % extractables | |
|---|---|---|
| Belt speed [m/min] | Example 6b | Comparative Experiment 4 |
| 100 | (2.70)* 2.5 | 7.8 |
| 150 | (1.80)* 5.0 | 16.2 |
| 200 | (1.35)* 10.0 | not cured |
| 250 | (1.08)* 19.2 | not cured |

*) residence time in the oven, in seconds

Under identical conditions, the novel formulation has cured much better (lower proportion of extracts). An acceptable limit of 5% extractables is achieved at only 65 m/rain by a customary formulation under given conditions, whereas the novel formulation can be applied rapidly, at a speed of up to 150 m/min.

EXAMPLE 8

Under the same conditions as in Example 7, the following formulations are tested in comparison (total SiH/C=C is 2.0):

| | Example 6b | | Comparative Experiment 4 | |
|---|---|---|---|---|
| | g | meq | g | meq |
| α,Ω-Divinyl-PDMS | 2000 | 540 | 2000 | 540 |
| 1-Ethynylcyclohexanol | 5 | 40 | 5 | 40 |
| Carbosiloxane crosslinking agent 1 | 38 | 360 | — | — |
| Crosslinking agent $B^2$ | 47 | 720 | 70 | 1080 |
| Platinum catalyst | 21 | 1.0 | 21 | 1.0 |

| | % extractables | |
|---|---|---|
| Belt speed [m/min] | Example 6b | Comparative Experiment 4 |
| 100 | 2.2 | 2.5 |
| 150 | 3.7 | 5.2 |
| 200 | 6.3 | 11.0 |
| 250 | 10.6 | not cured |
| 300 | 16.8 | not cured |

Even at a higher level of the total quantity of crosslinking agent in comparison to Example 7, the novel formulation (Example 6b) shows much better curing under otherwise identical conditions.

What is claimed is:

1. A crosslinkable composition comprising (A) an organosilicon compound having radicals containing aliphatic carbon-carbon multiple bonds, (B) an organosilicon compound having Si-bonded hydrogen atoms, (C) a catalyst which promotes the addition of Si-bonded hydrogen onto aliphatic multiple bond, and, optionally, (D) an agent which retards the addition of Si-bonded hydrogen onto aliphatic multiple bond at room temperature, wherein at least one (B) organosilicon compound having Si-bonded hydrogen atoms is an organosilicon compound ($B^1$) comprising (a) terminal units of the formula $$H_a R_{3-a} SiO_{1/2} \quad (I)$$

and, optionally, terminal units of the formula $$R_3 SiO_{1/2} \quad (I')$$

in which

R is an identical or different monovalent, optionally halogenated hydrocarbon radical having 1 to 8 carbon atoms per radical and is free from aliphatic multiple bonds, and a is 1, 2 or 3, with the proviso that at least 50 mole % of the terminal units are those of formula (I), (b) carbo-structural units G (II)

in which

G is an identical or different divalent to decavalent aliphatic hydrocarbon radical having 2 to 30 carbon atoms per radical optionally containing one or more heteroatoms selected from the group consisting of oxygen, boron, silicon, tin and titanium, with the proviso that at least two Si atoms are connected to one another via G, (c) units of the formulae $$R_b \underset{|}{Si} O_{\frac{3-b}{2}}, \quad (III)$$

or $$R_b \underset{|}{Si} O_{\frac{2-b}{2}} \quad (III')$$

or mixtures thereof, in which

R is as defined above, and b is 0, 1 or 2, with the provisos that b in formula (III') is not 2 and the units of formula (III) or (III') are connected via the Si atoms to the carbo-structural units G, and, optionally, (d) units of the formula $$H_c R_d SiO_{\frac{4-c-d}{2}} \quad (IV)$$

in which

R is as defined above, c is 0 or 1 and d is 1 or 2 and the sum c+d is 1 or 2, with the proviso that the units of formula (IV) are located between the units of formula (III) or (III') and the terminal units of formulae (I) or (I'), and with the proviso that the organosilicon compounds ($B^1$) on average contain 8 to 50 Si-bonded hydrogen atoms per molecule.

2. A crosslinkable composition as claimed in claim 1, wherein the organosilicon compounds ($B^1$) is prepared in a first step, by reacting aliphatic hydrocarbon compounds (1) having aliphatic multiple bonds and 2 to 30 carbon atoms, and optionally containing one or more heteroatoms selected from the group consisting of oxygen, boron, silicon, tin and titanium, with silanes (2) of the formula $$HSR_bSiX_{3-b}$$

in which

R is an identical or different monovalent, optionally halogenated hydrocarbon radical having 1 to 8 carbon atoms per radical and is free from aliphatic multiple bonds, and X is an identical or different halogen atom or a radical of the formula —$OR^1$ in which $R^1$ is an alkyl radical having 1 to 8 carbon atoms per radical, which is optionally substituted by an ether oxygen atom, and b is 0, 1 or 2, in the presence of catalysts (3) which promote the addition of Si-bonded hydrogen onto aliphatic multiple bond and removing excess silanes (2) by distillation, the ratio of Si-bonded hydrogen in silane (2) to aliphatic double bond in hydrocarbon compound (1) being from 1.0 to 2.0, and to aliphatic triple bond in hydrocarbon compound (1) being from 2.0 to 4.0, in a second step, reacting the compounds of step one, containing hydrolyzable groups, with silanes (4) of the formula $$H_aR_{3-a}SiZ$$

or siloxanes (5) of the formula $$H_aR_{3-a}SiOSiR_{3-a}H_a$$

in which

R is as defined above and

Z is a halogen atom or a radical of the formula —$OR^2$ in which $R^2$ is a monovalent hydrocarbon radical having 1 to 8 carbon atoms per radical, which is optionally substituted by an ether oxygen atom, and a is 1, 2 or 3, and water in the presence of catalysts (6) which promote hydrolysis, the ratio used of Si atoms in silanes (4) or siloxanes (5) to hydrolyzable groups in the compounds obtained from the first step being from 0.8 to 5.0, and, optionally, in a third step, equilibrating the organosilicon compounds of step two having Si-bonded hydrogen atoms with organopolysiloxanes (7) which optionally contain Si-bonded hydrogen atoms and are selected from the group consisting of linear organopolysiloxanes containing terminal triorganosiloxy groups, linear organopolysiloxanes containing terminal hydroxyl groups, branched organopolysiloxanes optionally containing hydroxyl groups, cyclic organopolysiloxanes, and copolymers comprising diorganosiloxane and monoorganosiloxane units, with the proviso that the organosilicon compounds (B) thus obtained, having Si-bonded hydrogen atoms, possess on average 8 to 50 Si-bonded hydrogen atoms per molecule.

3. A coating which repels tacky substances comprising a crosslinkable composition as claimed in claim 1.

4. An organosilicon compound ($B^1$) having Si-bonded hydrogen atoms and comprising (a) terminal units of the formula $$H_aR_{3-a}SiO_{1/2} \qquad (I)$$

and, optionally, terminal units of the formula $$R_3SiO_{1/2} \qquad (I')$$

in which

R is an identical or different monovalent, optionally halogenated hydrocarbon radical which has 1 to 15 carbon atoms per radical and is free from aliphatic multiple bonds, and a is 1, 2 or 3, (b) carbo-structural units G (II)

in which

G is an identical or different divalent to decavalent aliphatic hydrocarbon radical having 2 to 30 carbon atoms per radical optionally containing one or more heteroatoms selected from the group consisting of oxygen, boron, silicon, tin and titanium, with the proviso that at least two Si atoms are connected to one another via G, (c) units of the formulae $$R_bSiO_{\frac{3-b}{2}} \qquad (III)$$

or $$R_bSiO_{\frac{2-b}{2}} \qquad (III')$$

or mixtures thereof in which

R is as defined above, and b is 0, 1 or 2, with the provisos that b in formula (III') is not 2 and the units of formula (III) or (III') are connected via the Si atoms to the carbostructural units G, and, optionally, (d) units of the formula $$H_cR_dSiO_{\frac{4-c-d}{2}} \qquad (IV)$$

in which

R is as defined above,

C is 0 or 1 and d is 1 or 2 and the sum c+d is 1 or 2, with the proviso that the units of formula (IV) are located between the units of formula (III) or (III') and the terminal units of the formula (I) or (I'), and the organosilicon compound ($B^1$) on average contains 8 to 50 Si-bonded hydrogen atoms per molecule.

5. An organosilicon compound ($B^1$) having Si-bonded hydrogen atoms as claimed in claim 4, wherein b is 0 or 1.

6. A process for preparing an organosilicon compound ($B^1$) having Si-bonded hydrogen atoms, as claimed in claim 4, comprising in a first step, reacting aliphatic hydrocarbon compounds (1) having aliphatic multiple bonds and 2 to 30 carbon atoms, and optionally one or more heteroatoms selected from the group consisting of oxygen, boron, silicon, tin and titanium, with silanes (2) of the formula $HR_bSiX_{3-b}$ in which R is an identical or different monovalent, optionally halogenated hydrocarbon radical having 1 to 8 carbon atoms and is free from aliphatic multiple bonds, and X is an identical or different halogen atom or a radical of the formula —$OR^1$ in which $R^1$ is an alkyl radical having 1 to 8 carbon atoms per radical, optionally substituted by an ether oxygen atom, and b is 0, 1 or 2, in the presence of catalysts (3) which promote the addition of Si-bonded hydrogen onto aliphatic multiple bond and removing excess silanes (2) by distillation, the ratio used of Si-bonded hydrogen in silane (2) to aliphatic double bond in hydrocarbon compound (1) being from 1.0 to 2.0, and to aliphatic triple bond in hydrocarbon compound (1) being from 2.0 to 4.0, in a second step reacting the compounds of step one, containing hydrolyzable groups, with silanes (4) of the formula $H_aR_{3-a}SiZ$ or siloxanes (5) of the formula $H_aR_{3-a}SiOSiR_{3-a}H_a$ in which R is as defined above and Z is a halogen atom or a radical of the formula —$OR^2$ in which $R^2$ is a monovalent hydrocarbon radical having 1 to 8 carbon atoms per radical which is optionally substituted by an ether oxygen atom, and a is 1, 2 or 3, and water in the presence of catalysts (6) which promote hydrolysis, the ratio used of Si atoms in silanes (4) or siloxanes (5) to hydrolyzable groups in the compounds obtained from the first step being from 0.8 to 5.0, and, optionally, in a third step equilibrating the organosilicon compounds of step two having Si-bonded hydrogen atoms with organopolysiloxanes (7) which optionally contain Si-bonded hydrogen atoms and which are selected from the group consisting of linear organopolysiloxanes containing terminal triorganosiloxy groups, linear organopolysiloxanes containing terminal hydroxyl groups, branched organopolysiloxanes optionally containing hydroxyl groups, cyclic organopolysiloxanes, and copolymers comprising diorganosiloxane and monoorganosiloxane units, with the proviso that the organosilicon compound ($B^1$) thus obtained, having Si-bonded hydrogen atoms, possess on average 8 to 50 Si-bonded hydrogen atoms per molecule.

7. The process as claimed in claim 6, wherein the hydrocarbon compound (1) used is 1,2,4-trivinylcyclohexane.

* * * * *